United States Patent
Iwasaka

[11] Patent Number: 5,885,207
[45] Date of Patent: Mar. 23, 1999

[54] FLEXIBLE TUBE OF ENDOSCOPE

[75] Inventor: Kikuo Iwasaka, Tokyo, Japan

[73] Assignee: Asahi Kogaku Kogyo Kabushiki Kaisha, Tokyo, Japan

[21] Appl. No.: 959,077

[22] Filed: Oct. 28, 1997

[30] Foreign Application Priority Data

Nov. 1, 1996 [JP] Japan .................................. 8-291515

[51] Int. Cl.⁶ .................................................. A61B 1/005
[52] U.S. Cl. ........................................... 600/139; 600/140
[58] Field of Search .................... 600/139, 140, 600/143

[56] References Cited

U.S. PATENT DOCUMENTS

| | | | |
|---|---|---|---|
| 3,670,721 | 6/1972 | Fukami | 600/140 |
| 3,998,216 | 12/1976 | Hosono et al. | 600/140 |
| 4,236,509 | 12/1980 | Takahashi et al. | 600/139 |
| 4,495,134 | 1/1985 | Ouchi et al. | . |
| 4,676,229 | 6/1987 | Krasnicki et al. | 600/140 |
| 4,690,175 | 9/1987 | Ouchi et al. | 600/140 |
| 4,714,075 | 12/1987 | Krauter et al. | 600/140 |
| 4,753,222 | 6/1988 | Morishita | 600/140 |
| 4,899,787 | 2/1990 | Ouchi et al. | 600/140 |
| 4,944,287 | 7/1990 | Takahashi et al. | . |
| 5,058,567 | 10/1991 | Takahashi et al. | 600/139 |
| 5,217,002 | 6/1993 | Katsurada et al. | . |
| 5,275,152 | 1/1994 | Krauter et al. | 600/140 |
| 5,394,864 | 3/1995 | Kobayashi et al. | . |
| 5,685,825 | 11/1997 | Takase et al. | 600/140 |

FOREIGN PATENT DOCUMENTS 63-11011  3/1988  Japan .
3-42896   6/1991  Japan .

*Primary Examiner*—Paul J. Hirsch
*Attorney, Agent, or Firm*—Greenblum & Bernstein, P.L.C.

[57] ABSTRACT

A flexible tube of an endoscope includes a tubular spiral, a meshwork tube provided around the tubular spiral, and a resin sheath provided around the meshwork tube. The meshwork tube is made by netting a plurality of wire bundles, each of the bundles being made of a plurality of metal wires. At least one wire for each bundle is coated with a coating material made of thermoplastic resin. The coating material is bonded to the resin sheath and the tubular spiral by heating the resin sheath and the meshwork tube.

19 Claims, 3 Drawing Sheets

FLEXIBLE TUBE OF ENDOSCOPE

BACKGROUND OF THE INVENTION

This invention relates to a flexible tube of an endoscope.

An endoscope is provided with a flexible tube which is inserted into a human body cavity. In order to obtain the flexibility, the flexible tube includes a tubular spiral made of a metal band wound in helical fashion. In order to maintain the wound shape of the metal band of the tubular spiral, a meshwork tube is provided around the tubular spiral to cover the tubular spiral. A resin sheath is adhered to the outer surface of the meshwork tube, thereby to surround the meshwork tube.

However, when the flexible tube is bent, a stress is applied to the resin sheath at the bent portion of the flexible tube. Therefore, the resin sheath may be separated from the meshwork tube, which causes buckling of the resin sheath. Thus, the durability of the flexible tube may be lowered.

Further, since a stress is also applied to the resin sheath at the bent portion of the flexible tube, the meshwork tube may be separated from the tubular spiral, so that the wound shape of the metal band may not be maintained. Thus, the flexibility of the flexible tube may be lowered.

SUMMARY OF THE INVENTION

It is therefore an object of the present invention to improve the durability and the flexibility of the flexible tube.

According to one aspect of the present invention, there is provided a flexible tube including a tubular spiral, a meshwork tube provided around the tubular spiral, and a resin sheath provided around the meshwork tube. The meshwork tube is made of a plurality of metal wires. At least one of the wires is coated with a coating material made of thermoplastic resin. The coating material is bonded to at least one of the resin sheath and the tubular spiral by heating the coating material. Preferably, the coating material is bonded to both of the resin sheath and the tubular spiral.

With such an arrangement, since the resin sheath is bonded to the meshwork tube, the resin sheath is not separated from the meshwork tube even when the flexible tube is bent. Thus, the buckling of the resin sheath can be prevented, which improves the durability of the flexible tube. Further, since the meshwork tube is bonded to the tubular spiral, the wound shape of the tubular spiral is maintained. Thus, the flexibility of the flexible tube is improved.

In a preferred arrangement, the meshwork tube is made by netting a plurality of wire bundles. Each wire bundle is made of a plurality of metal wires. In this case, it is possible that at least one wire for each bundle is coated with the coating material.

It is preferred that the coating material and the resin sheath are made of the same thermoplastic resin. With this, the same coating material is easily bonded to the resin sheath by heating.

Further, the tubular spiral is made of a metal band which is wound in helical fashion. The wire bundle is so made that respective metal wires are aligned in parallel with each other. Thus, the coating material can be easily adhered to the surface of the metal band of the tubular spiral.

According to another aspect of the invention, there is provided a method for manufacturing the flexible tube including the steps of (1) providing the meshwork tube around the tubular spiral, (2) providing the resin sheath around the meshwork tube, and (3) heating the resin sheath and the meshwork tube so that the coating material is molten and bonded to at least one of the resin sheath and the tubular spiral.

DESCRIPTION OF THE PREFERRED EMBODIMENT

The embodiment of the present invention is described with reference to the accompanying drawings.

Figure 1:
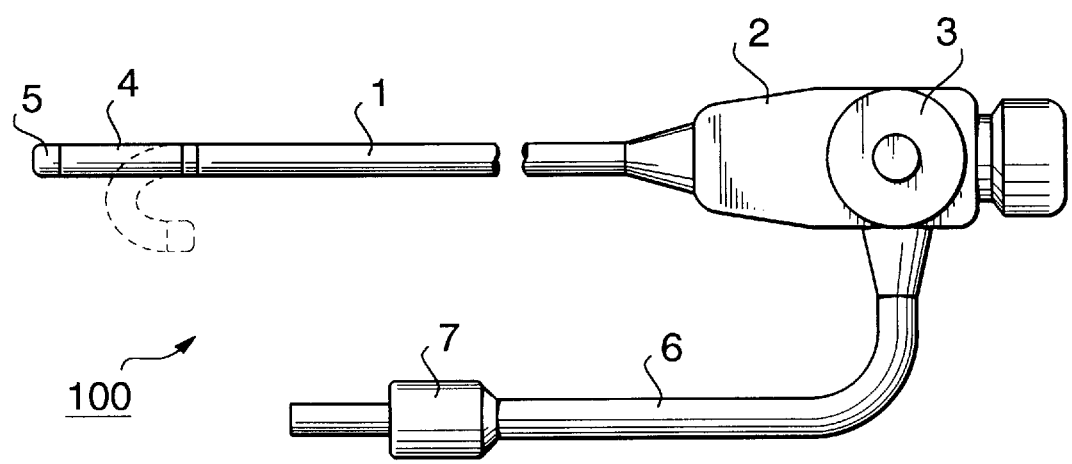
FIG. 1 is a side view of an endoscope in which a flexible tube of the invention is employed.

FIG. 1 is a side view of an endoscope in which a flexible tube of the invention is employed. As shown in FIG. 1, an endoscope 100 includes a flexible tube 1 which is to be inserted into a human body cavity and a manipulating portion 2. The flexible tube 1 has a bending portion 4 at the distal end thereof, which is arranged to be freely bent (as shown by dash-line in FIG. 1) and is remotely manipulated by a knob 3 provided to the manipulating portion 2. Components such as an objective system (not shown) are accommodated in a tip 5 of the free-bending portion 4. The manipulating portion 2 is further provided with a cable 6 having a connector 7 which is connected to a light source (not shown).

Figure 2:
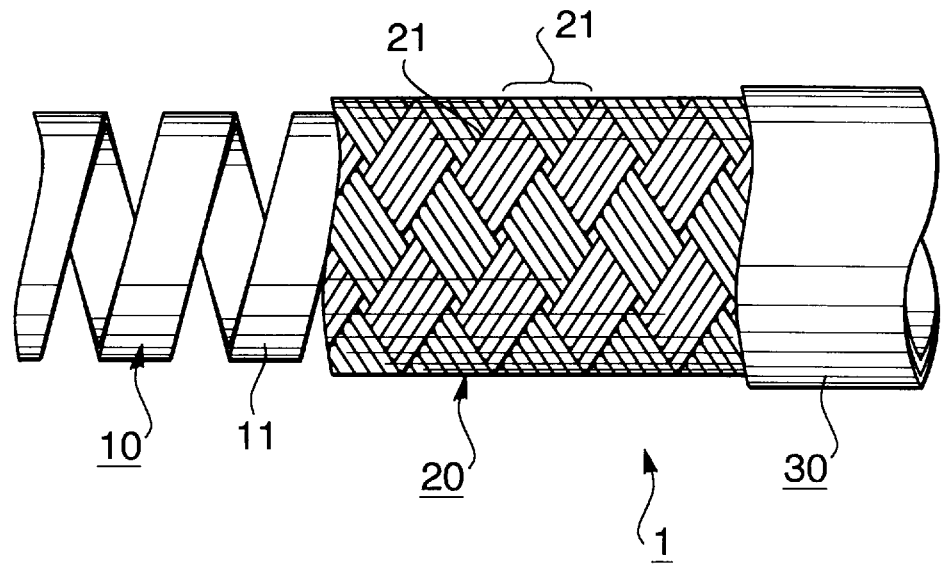
FIG. 2 is a partially-cutaway side view of a flexible tube of an endoscope.

FIG. 2 is a partially-cutaway side view of the flexible tube 1. The flexible tube 1 includes a inner tubular spiral 10, a meshwork tube 20 covering the inner tubular spiral 10, and a resin sheath 30 covering the meshwork tube 20.

In order to obtain the flexibility, the tubular spiral 10 is made of a metal band 11 which is wound in helical fashion. The metal band 11 is made of stainless-steel, copper alloy or the like.

The meshwork tube 20 is provided to maintain the wound shape of the metal band 11 of the tubular spiral 10. The meshwork tube 20 is made by netting wire bundles 21. Each wire bundle 21 is made of several (for example, four to twelve) metal wires 21a (FIG. 3) bundled so that the respective metal wires are aligned in parallel with each other. The metal wire is made of stainless-steel, copper alloy or the like. The meshwork tube 20 is fixed to the tubular spiral 10 at the longitudinal ends of the flexible tube 1, by means of soldering.

The resin sheath 30 is adhered to the outer surface of the meshwork tube 20. The resin sheath 30 is made of a thermoplastic resin (such as polyurethane) and is formed by means of extrusion, dipping, tube coating or the like.

Figure 3:
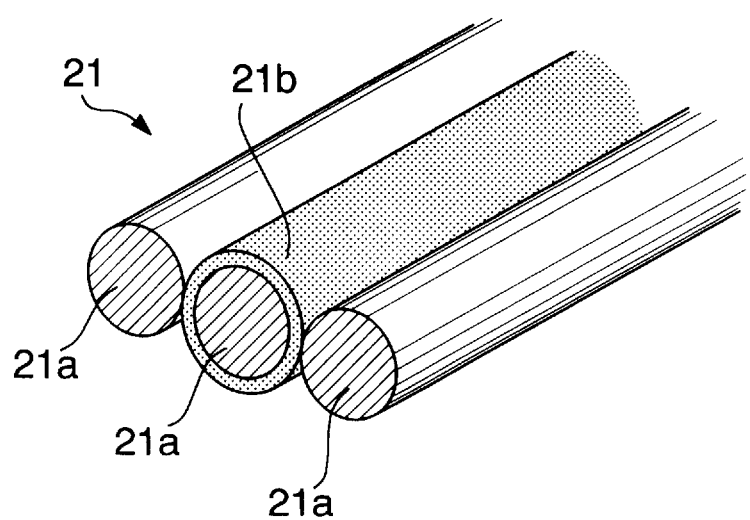
FIG. 3 is a sectional view showing a wire bundle of a meshwork tube of the flexible tube of FIG. 2.

FIG. 3 is a sectional view showing three wires 21a which belong to one wire bundle 21. One of the wires 21a is coated with a coating material 21b throughout the length of the wire 21a. The coating material 21b is made of the same thermoplastic resin as the resin sheath 30.

In the manufacturing process of the flexible tube 1, after the resin sheath 30 is provided around the meshwork tube 20, the resin sheath 30 and the meshwork tube 20 are heated so that the coating material 21b of the wire 21a and the resin sheath 30 are molten. The molten portions of the coating material 21*b* and the resin sheath 30 are integrated. Thus, the resin sheath 30 is securely bonded to the meshwork tube 20 throughout the length of the flexible tube 1. Accordingly, even when the flexible tube 1 is bent, the resin sheath 30 is not separated from the meshwork tube 20. Further, the molten portion of the coating material 21*b* is also bonded to the metal band 11 of the tubular spiral 10 (FIG. 2). Thus, the meshwork tube 20 is not separated from the tubular spiral 10.

As constructed above, according to the embodiment, since the resin sheath 30 is bonded to the meshwork tube 20, the resin sheath 30 is not separated from the meshwork tube 20 even when the flexible tube 1 is bent. Thus, the buckling of the resin sheath 30 can be prevented, which improves the durability of the flexible tube 1. Further, since the meshwork tube 20 is bonded to the tubular spiral 10, the wound shape of the tubular spiral 10 is maintained. Thus, the flexibility of the flexible tube 2 is improved.

It is alternatively possible that a plurality of wires 21*a* belonging to each wire bundle 21 are coated with the coating material 21*b*. It is also possible that all the wires 21*a* are coated with the coating material 21*b*. Further, as long as the coating 21 is made of thermoplastic resin, it is possible that the coating 21 is made of different material from the resin sheath 30.

Figure 4:
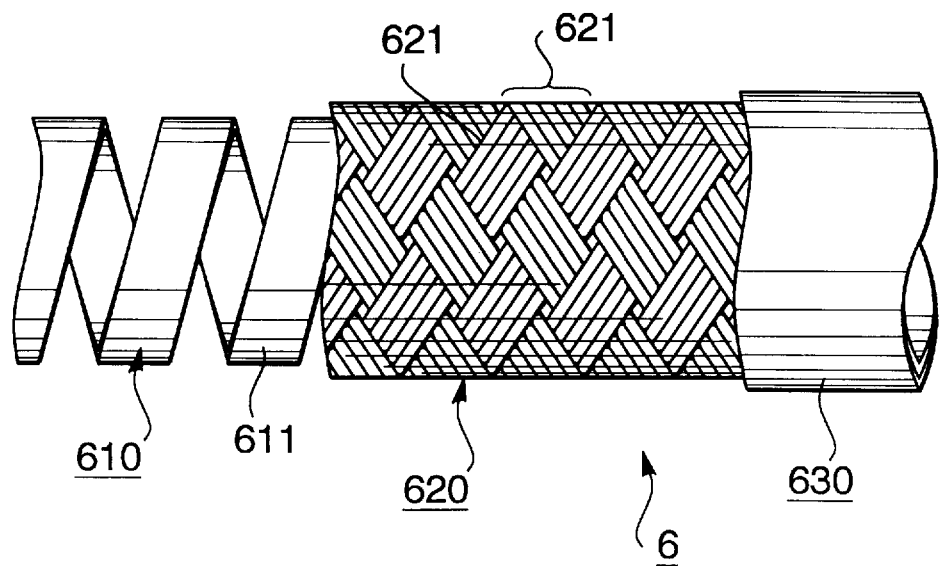
FIG. 4 is a partially-cutaway side view of a cable of an endoscope.
Figure 5:
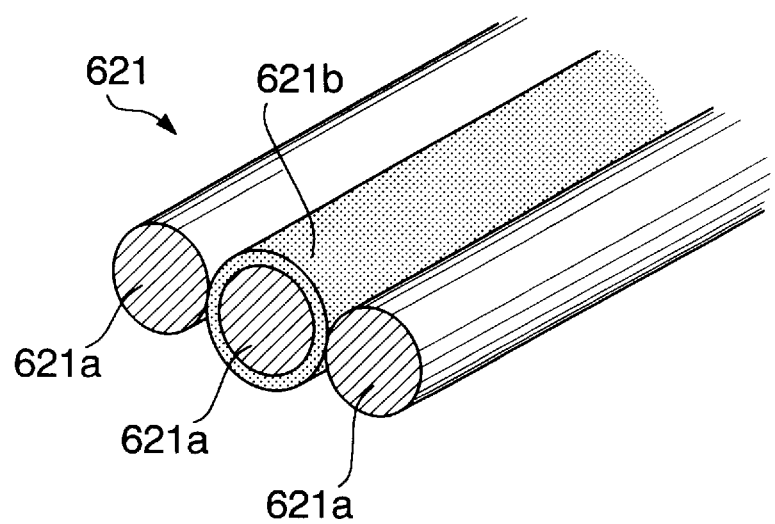
FIG. 5 is a sectional view showing a wire bundle of a meshwork tube of the cable of FIG. 4.

In this embodiment, the structure of the flexible tube 1 is adapted to a sheath of the cable 6. FIG. 4 is a partially-cutaway side view of the cable 6. As shown in FIG. 4, the cable 6 includes a tubular spiral 610, a meshwork tube 620 provided around the tubular spiral 610, and a resin sheath 630 provided around the meshwork tube 620. The meshwork tube 620 is made by netting wire bundles 621. FIG. 5 is a sectional view showing three wires 621*a* which belong to one wire bundle 621. As shown in FIG. 5, the meshwork tube 620 is made of a plurality of metal wires 621. One of the wires 621*a* is coated with a coating material 621*b* made of thermoplastic resin. The coating material is bonded to the resin sheath 630 and the tubular spiral 610 by heating the coating material. With such an arrangement, the durability and the flexibility of the cable 6 are improved.

Although the structure of a flexible tube is described herein with respect to the preferred embodiment, many modifications and changes can be made without departing from the spirit and scope of the invention.

The present disclosure relates to subject matter contained in Japanese Patent Application No. HEI 08-291515 filed on Nov. 1, 1996 which is expressly incorporated herein by reference in its entirety.

What is claimed is:

1. A flexible tube for an endoscope, comprising:

a tubular spiral;

a meshwork tube provided around said tubular spiral, said meshwork tube being made of a plurality of metal wires; and a resin sheath provided around said meshwork tube;

at least one of said wires being coated with a coating material made of thermoplastic, wherein said coating material is bonded to at least said resin sheath by heating said coating material.

2. The flexible tube according to claim 1, wherein said coating material is bonded to both of said resin sheath and said tubular spiral by heating said coating material and said meshwork tube.

3. The flexible tube according to claim 1, wherein said meshwork tube is made by netting a plurality of wire bundles, each of said bundles being made of a plurality of metal wires, and wherein at least one wire for each bundle is coated with said coating material.

4. The flexible tube according to claim 1, wherein said coating material and said resin sheath are made of same thermoplastic resin.

5. The flexible tube according to claim 1, wherein said tubular spiral is made of a metal band which is wound in helical fashion.

6. The flexible tube according to claim 3, said bundle is so made that respective metal wires are aligned in parallel with each other.

7. A method for manufacturing the flexible tube of claim 1, said method comprising the steps of:

providing said meshwork tube around said tubular spiral;

providing said resin sheath around said meshwork tube; and heating said resin sheath and said meshwork tube so that said coating material is molten and bonded to said resin sheath and said tubular spiral.

8. An endoscope unit including the flexible tube of claim 1, further comprising a cable which transmits light from a light source to said flexible tube, said cable comprising:

a tubular spiral;

a meshwork tube provided around said tubular spiral, said meshwork tube being made of a plurality of metal wires; and a resin sheath provided around said meshwork tube;

at least one of said wires being coated with a coating material made of thermoplastic, wherein said coating material is bonded to at least one of said resin sheath and said tubular spiral by heating said coating material.

9. The flexible tube according to claim 1, wherein said coating material on said at least one wire is provided thereon prior to forming said meshwork tube.

10. The flexible tube according to claim 9, wherein said coating surrounds the outer diameter of each said at least one wire throughout the length thereof.

11. The flexible tube according to claim 1, wherein said at least one wire has an individual coating of material throughout the length thereof.

12. A flexible tube for an endoscope, comprising:

a tubular spiral;

a meshwork tube provided around said tubular spiral, said meshwork tube being made by netting a plurality of wire bundles, each of said bundles being made of a plurality of metal wires; and a resin sheath provided around said meshwork tube;

at least one wire for each bundle being coated with a coating material made of thermoplastic resin, wherein said coating material is bonded to said resin sheath and said tubular spiral by heating said resin sheath and said meshwork tube.

13. The flexible tube according to claim 12, wherein said tubular spiral is made of a metal band which is wound in helical fashion.

14. The flexible tube according to claim 12, each said bundle is so made that respective metal wires are aligned in parallel with each other.

15. The flexible tube according to claim 12, wherein said coating material and said resin sheath are made of same thermoplastic resin.

16. A method for manufacturing the flexible tube of claim 15, said method comprising the steps of:

providing said meshwork tube around said tubular spiral;

providing said resin sheath around said meshwork tube; and heating said resin sheath and said meshwork tube so that said coating material is molten and bonded to said resin sheath and said tubular spiral.

17. The flexible tube according to claim 12, wherein said coating material on said at least one wire of each said bundle is provided thereon prior to forming said bundles.

18. The flexible tube according to claim 17, wherein said coating material of said wire of each said bundle surrounds the outer diameter of each said at least one wire throughout the length thereof.

19. The flexible tube according to claim 12, wherein said at least one wire of each said bundle has an individual coating of material throughout the length thereof.

* * * * *